(12) United States Patent
He

(10) Patent No.: US 11,478,575 B1
(45) Date of Patent: Oct. 25, 2022

(54) REMOVAL DEVICE FOR REMOVING OBSTRUCTION IN RESPIRATORY TRACT AND CONNECTOR

(71) Applicant: DCSTAR INC, New York, NY (US)

(72) Inventor: Ligui He, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 17/393,249

(22) Filed: Aug. 3, 2021

(51) Int. Cl.
| | |
|---|---|
| A61M 1/00 | (2006.01) |
| A61B 17/24 | (2006.01) |
| A61B 17/50 | (2006.01) |
| A61M 16/00 | (2006.01) |
| A61M 16/20 | (2006.01) |

(52) U.S. Cl.
CPC ............... *A61M 1/00* (2013.01); *A61B 17/24* (2013.01); *A61B 17/50* (2013.01); *A61M 1/67* (2021.05); *A61M 16/00* (2013.01); *A61M 16/20* (2013.01); *A61M 2205/3337* (2013.01)

(58) Field of Classification Search
CPC .......... A61M 16/0003; A61M 16/0057; A61M 16/0063; A61M 16/0075; A61M 16/0084; A61M 16/08; A61M 16/201; A61M 16/206; A61M 16/208–209; A61M 1/00; A61M 1/67; A61M 2205/075; A61M 3/0262; A61B 17/24; A61B 17/50
USPC ................................................ 128/200, 205
See application file for complete search history.

(56) References Cited

U.S. PATENT DOCUMENTS

| | | | | |
|---|---|---|---|---|
| 3,316,903 A | * | 5/1967 | Richards | A61M 16/0084 128/205.16 |
| 4,196,728 A | | 4/1980 | Granite | |
| 4,971,053 A | * | 11/1990 | Tarrats | A61B 17/50 128/206.28 |
| 6,145,135 A | * | 11/2000 | Pool | E03C 1/308 4/255.09 |
| 7,219,668 B2 | * | 5/2007 | Flynn | A61M 16/0084 128/205.13 |
| 7,351,245 B2 | * | 4/2008 | Rozinsky | A61M 16/0463 606/106 |

(Continued)

OTHER PUBLICATIONS

Idear, 3Packs Anti Choking Device for Family, Effective Choking Rescue Device, Easy-to-Use & Portable Suction Choking Kit for Adult & Kids, Dislodge Obstructor in Airway, Essential First Aid Kit for Homes, Amazon (2021) (Year: 2021).*

*Primary Examiner* — Justine R Yu
*Assistant Examiner* — Kelsey E Baller
(74) *Attorney, Agent, or Firm* — Hamre, Schumann, Mueller & Larson, P.C.

(57) ABSTRACT

A removal device includes a collapsible gasbag, a connector and a face mask, wherein the collapsible gasbag is provided with a gas storage cavity and an opening; the connector is connected to the opening, and the connector is provided with a first check valve and a second check valve; a first gas outlet end of the first check valve is in communication with the gas storage cavity, a second gas inlet end of the second check valve is in communication with the gas storage cavity, and a second gas outlet end of the second check valve is in communication with the outside; and the face mask is connected to a first gas inlet end of the first check valve, and the face mask is provided with a flexible annular pad.

17 Claims, 4 Drawing Sheets

(56) References Cited

U.S. PATENT DOCUMENTS

| | | |
|---|---|---|
| 9,932,936 B2 | 4/2018 | Klonis et al. |
| 10,271,998 B2 | 4/2019 | LaVon et al. |
| 10,675,393 B1* | 6/2020 | Carver .................. A61B 17/24 |
| 2009/0228018 A1* | 9/2009 | Winiarski ............. A61M 1/804 |
| | | 606/106 |
| 2011/0197892 A1* | 8/2011 | Koledin ............ A61M 16/0866 |
| | | 128/205.24 |
| 2015/0190158 A1* | 7/2015 | Li ...................... A61M 16/0075 |
| | | 606/106 |
| 2018/0099108 A1* | 4/2018 | Baek ................. A61M 16/0063 |
| 2020/0306420 A1* | 10/2020 | Carver .................. A61M 1/962 |

\* cited by examiner

REMOVAL DEVICE FOR REMOVING OBSTRUCTION IN RESPIRATORY TRACT AND CONNECTOR

TECHNICAL FIELD

The disclosure relates to the technical field of medical instruments, and in particular to a removal device for removing an obstruction in a respiratory tract and a connector.

BACKGROUND

Asphyxiation caused by an obstruction in a respiratory tract will often cause the breathing to stop and is fatal, if first aid is not given within 4-6 minutes; and even if the life is saved, it will often cause irreversible damage due to lack of oxygen for an excessively long time. Therefore, in the rescue, it is necessary to race against the clock to remove the respiratory tract obstruction due to various causes, to make the airway unblocked, ensure that the wounded can be evacuated in a timely and safe manner, and provide the wounded with opportunities of further treatment.

At present, "Heimlich Maneuver" is usually used to give the first aid to the patient with the respiratory tract obstruction. However, the public may cannot implement the "Heimlich Maneuver" first aid method correctly without training, which leads to death of the patient with the respiratory tract obstruction caused by choking.

SUMMARY

The technical problem to be solved by the disclosure is to provide a removal device for removing an obstruction in a respiratory tract which is simple in structure and operation and practically effective. The removal device is a backup device and a safety guarantee when the "Heimlich Maneuver" rescue method may not be implemented effectively or there is no others around for help. In addition, if your own respiratory tract suffers obstruction and choking, the removal device may be utilized for self-rescue without the help of others around.

The other technical problem to be solved by the disclosure is to provide a connector used for the above removal device.

To solve the above technical problem, a technical solution used by the disclosure is to provide a removal device for removing an obstruction in a respiratory tract. The removal device comprises a collapsible gasbag, a connector and a face mask which are sequentially connected, wherein the collapsible gasbag is internally provided with a gas storage cavity, the top of the collapsible gasbag is sealed, and the bottom of the collapsible gasbag is provided with an opening in communication with the gas storage cavity; an upper side of the connector is hermetically connected to the opening, and the connector is provided with a first check valve and a second check valve; a first gas outlet end of the first check valve is in communication with the gas storage cavity, a second gas inlet end of the second check valve is in communication with the gas storage cavity, and a second gas outlet end of the second check valve is in communication with the outside; and an upper side of the face mask is hermetically connected to a first gas inlet end of the first check valve, and a lower side of the face mask is provided with a flexible annular pad attached to a face.

When the removal device of the above technical solution is used, the flexible annular pad of the face mask may encircle a mouth of a choked patient and be closely attached to a face, so as to be connected to a respiratory tract of the patient; and then, the face mask is held with one hand to keep a seal between the face mask and the face, and the collapsible gasbag is pressed downward and stretched with the other hand repeatedly, such that the obstruction in the respiratory tract of the patient may be extracted out quickly. In the process of compressing the collapsible gasbag, gas in the gas storage cavity may be discharged to the outside through the second check valve, but may not enter the respiratory tract of the patient through the first check valve. In the process of stretching the collapsible gasbag, the volume of the gas storage cavity increases, and the second check valve may prevent the outside gas from flowing into the gas storage cavity, so as to form negative pressure in the gas storage cavity, that is, gas pressure in the gas storage cavity is lower than gas pressure in the respiratory tract of the patient, such that the gas pressure in the respiratory tract may push the obstruction outward, and thus discharge the obstruction out.

In the removal device for removing an obstruction in a respiratory tract provided by the disclosure, the connector is provided with a plurality of second check valves, the plurality of second check valves encircling the first check valve. By arranging the plurality of second check valves, the discharge velocity of the gas in the gas storage cavity may be accelerated when the collapsible gasbag is compressed, which is conducive to improving the efficiency of downward pressing of the collapsible gasbag.

In the removal device for removing an obstruction in a respiratory tract provided by the disclosure, the connector is provided with a bottom plate, the bottom plate being provided with a central cylinder which is vertically through; the first check valve is of a hollowed structure made from an elastic material, and comprises a deformed portion and a first base portion which are connected to each other; the first gas outlet end is composed of at least three first slits provided at a top end of the deformed portion; one ends, extending toward the center, of the at least three first slits intersect at the same point, and the first gas inlet end is a first vent hole provided in the middle of the first base portion; the first base portion extends into the central cylinder, and an outer side of the first base portion is hermetically connected to an inner side of the central cylinder; a lower end of the central cylinder is hermetically connected to an upper side of the face mask; the deformation portion is exposed out of the central cylinder and extends into the gas storage cavity; when gas flows into the deformation portion through the first vent hole, pressure in the deformation portion gradually increases such that the deformation portion is deformed by expansion, so that the at least three first slits are opened, thereby allowing the gas on the side of the first vent hole to flow into the gas storage cavity; and when the gas flowing into the deformation portion through the first vent hole is reduced or disappears, pressure in the deformation portion is reduced and even reduced to zero, and the deformation portion shrinks under its own elasticity such that the three first slits are closed, thereby preventing the gas in the gas storage cavity from flowing out of the first vent hole.

In the removal device for removing an obstruction in a respiratory tract provided by the disclosure, the upper side of the face mask is provided with a connecting cylinder which is vertically through in the middle, the connecting cylinder being inserted into the inner side of the lower end of the central cylinder from bottom to top, and an outer side of the connecting cylinder being hermetically connected to the inner side of the central cylinder.

In the removal device for removing an obstruction in a respiratory tract provided by the disclosure, an upper side of the bottom plate is provided with a first peripheral side wall encircling the central cylinder, an upper end of the first peripheral side wall shrinking inward to form a stop edge; the collapsible gasbag is provided with a second peripheral side wall made from an elastic material, the second peripheral side wall being provided with a plurality of layers of outwardly convex folds; and the first peripheral side wall covers the lowermost fold of the second peripheral side wall, and the stop edge covers an upper side of the lowermost fold. Therefore, the connector and the collapsible gasbag are guaranteed to be connected stably, so as to prevent the connector from being separated from the collapsible gasbag.

In the removal device for removing an obstruction in a respiratory tract provided by the disclosure, a plurality of reinforcement strips are arranged on the upper side of the bottom plate, two opposite ends of each reinforcement strip being separately connected to the inner side of the first peripheral side wall and the outer side of the central cylinder. The reinforcement strip plays a role in stabilizing the connector, increasing the hardness of the connector, and therefore avoiding the situation that the first check valve or the second check valve deforms or components are not connected stably due to excessive deformation of the connector.

In the removal device for removing an obstruction in a respiratory tract provided by the disclosure, a top wall of the collapsible gasbag is connected to a handle for holding. In this way, the handle may be held to press or stretch the collapsible gasbag, facilitating application of force by a rescuer.

In the removal device for removing an obstruction in a respiratory tract provided by the disclosure, four first slits are provided, the four first slits being in the shape of a cross.

In the removal device for removing an obstruction in a respiratory tract provided by the disclosure, the connector is provided with a bottom plate, the bottom plate being provided with a peripheral cylinder which is vertically through; the second check valve is a duckbill valve, the second check valve comprises a duckbill portion and a second base portion which are connected to each other, the second gas inlet end is a second vent hole provided in the middle of the second base portion, and the second gas outlet end is a second slit provided in the duckbill portion; an outer side of the second base portion is hermetically connected to an inner side of the peripheral cylinder, and the second vent hole of the second base portion is in communication with the gas storage cavity; the duckbill portion extends into the peripheral cylinder, and a lower end of the peripheral cylinder is in communication with the outside; when gas flows into the duckbill portion through the second vent hole, pressure in the duckbill portion gradually increases such that the duckbill portion is deformed by expansion, so that the second slit is opened, thereby allowing gas in the gas storage cavity to be discharged to the outside; and when gas flowing into the duckbill portion through the second vent hole is reduced or disappears, pressure in the deformation portion is reduced and even reduced to zero, and the duckbill portion shrinks under its own elasticity such that the second slit is closed, thereby preventing outside gas from flowing into the gas storage cavity through the second vent hole.

In the removal device for removing an obstruction in a respiratory tract provided by the disclosure, the connector is an integrally formed member made from an elastic material. The connector may guarantee desirable gas impermeability of the connector itself as the integrally formed member, which is conducive to forming negative pressure in the gas storage cavity of the collapsible gasbag.

In the removal device for removing an obstruction in a respiratory tract provided by the disclosure, the face mask, the connector and the collapsible gasbag are integral.

In the removal device for removing an obstruction in a respiratory tract provided by the disclosure, the collapsible gasbag is not provided with a vent hole which is in direct communication with the outside.

To solve the other technical problem, according to a technical solution used by the disclosure, a connector for a removal device is provided. The connector comprises a bottom plate, and a first check valve and a second check valve which are arranged on the bottom plate, wherein the first check valve and the second check valve allow gas flow to pass in opposite directions; and the connector is an integrally formed member made from an elastic material.

In the connector provided by the disclosure, the connector is provided with one first check valve and a plurality of second check valves, the plurality of second check valves encircling the first check valve.

In the connector provided by the disclosure, the bottom plate is provided with a central cylinder which is vertically through; the first check valve is of a hollowed structure and comprises a deformed portion and a first base portion which are connected to each other, and a first gas outlet end and a second vent hole of the first check valve are provided in the deformed portion and the first base portion respectively; the first gas outlet end is composed of at least three first slits provided at a top end of the deformed portion, one ends, extending toward the center, of the at least three first slits intersecting at the same point; and the first gas inlet end is a first vent hole provided in the middle of the first base portion.

In the connector provided by the disclosure, the second check valve is a duckbill valve, the second check valve comprises a duckbill portion and a second base portion which are connected to each other, a second gas outlet end and a second gas inlet end of the second check valve are provided in the duckbill portion and the second base portion respectively; the second gas inlet end is a second vent hole provided in the middle of the second base portion; the second gas outlet end is a second slit provided in the duckbill portion; and the duckbill portion and the deformed portion separately face two opposite sides of the bottom plate.

In the connector provided by the disclosure, the removal device is the removal device mentioned above.

The removal device of the disclosure may at least achieve the following beneficial effects when implemented: the removal device comprises a collapsible gasbag, a connector and a face mask which are sequentially connected, wherein the collapsible gasbag is internally provided with a gas storage cavity, the top of the collapsible gasbag is sealed, and the bottom of the collapsible gasbag is provided with an opening in communication with the gas storage cavity; an upper side of the connector is hermetically connected to the opening, and the connector is provided with a first check valve and a second check valve; a first gas outlet end of the first check valve is in communication with the gas storage cavity, a second gas inlet end of the second check valve is in communication with the gas storage cavity, and a second gas outlet end of the second check valve is in communication with the outside; and an upper side of the face mask is hermetically connected to a first gas inlet end of the first check valve, and a lower side of the face mask is provided with a flexible annular pad attached to a face. When the removal device is used, the flexible annular pad of the face mask may encircle a mouth of a choked patient and be closely attached to a face, so as to be connected to a respiratory tract of the patient; and then, the face mask is held with one hand, so as to keep a seal between the face mask and the face, and the collapsible gasbag is quickly pressed downward and stretched with the other hand repeatedly, such that the obstruction in the respiratory tract of the patient may be extracted out. In this way, the removal device may be used as a backup device and a safety guarantee in the case of obstruction and choking rescue when the Heimlich Maneuver rescue method is ineffective or there is no others around for help.

BRIEF DESCRIPTION OF THE DRAWINGS

In order to more clearly explain the embodiments of the disclosure or the technical solutions in the prior art, the drawings to be used in the description of the embodiments or the prior art will be briefly introduced below. Obviously, the drawings in the following description are only embodiments of the disclosure. For those of ordinary skill in the art, other drawings may be obtained according to the provided drawings without any creative work.

Figure 1:
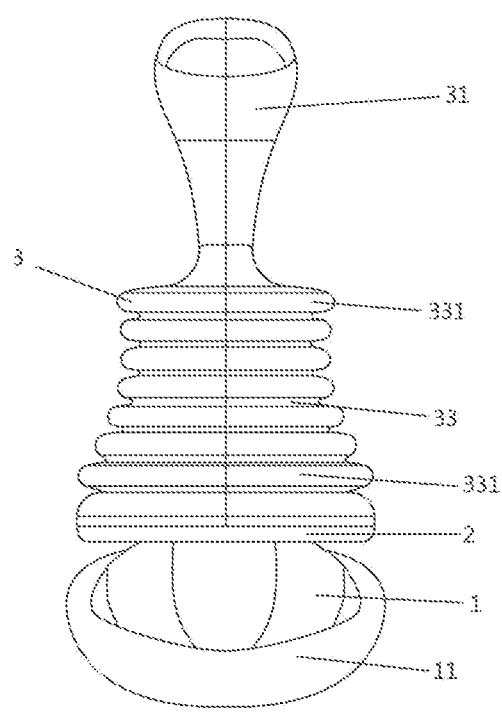
FIG. 1 is a three-dimensional combined schematic diagram of a removal device provided in this embodiment.

DESCRIPTION OF REFERENCE NUMERALS
IN SPECIFIC IMPLEMENTATIONS

| Face mask | 1 | Collapsible gasbag | 3 |
|---|---|---|---|
| Flexible annular pad | 11 | Handle | 31 |
| Connecting cylinder | 12 | Opening | 32 |
| Connector | 2 | Second peripheral side wall | 33 |
| First check valve | 21 | Second check valve | 22 |
| Bottom plate | 23 | First peripheral side wall | 24 |
| Peripheral cylinder | 25 | Central cylinder | 26 |
| Stop edge | 241 | Reinforcement strip | 27 |
| Deformed portion | 212 | First slit | 2121 |
| Duckbill portion | 222 | Second slit | 2221 |
| Second base portion | 221 | Fold | 331 |

DETAILED DESCRIPTION

In order to facilitate understanding of the disclosure, the disclosure will be described more comprehensively below with reference to related drawings. Typical embodiments of the disclosure are given in the drawings. However, the disclosure may be implemented in many different forms, which are not limited to the embodiments described herein. On the contrary, the purpose of providing these embodiments is to make the summary of the disclosure more thorough and comprehensive.

Unless otherwise defined, all technical and scientific terms used herein have the same meaning as commonly understood by those skilled in the technical field of the disclosure. The terms used in the specification of the disclosure herein is for the purpose of describing specific embodiments, and are not intended to limit the disclosure.

Figure 2:
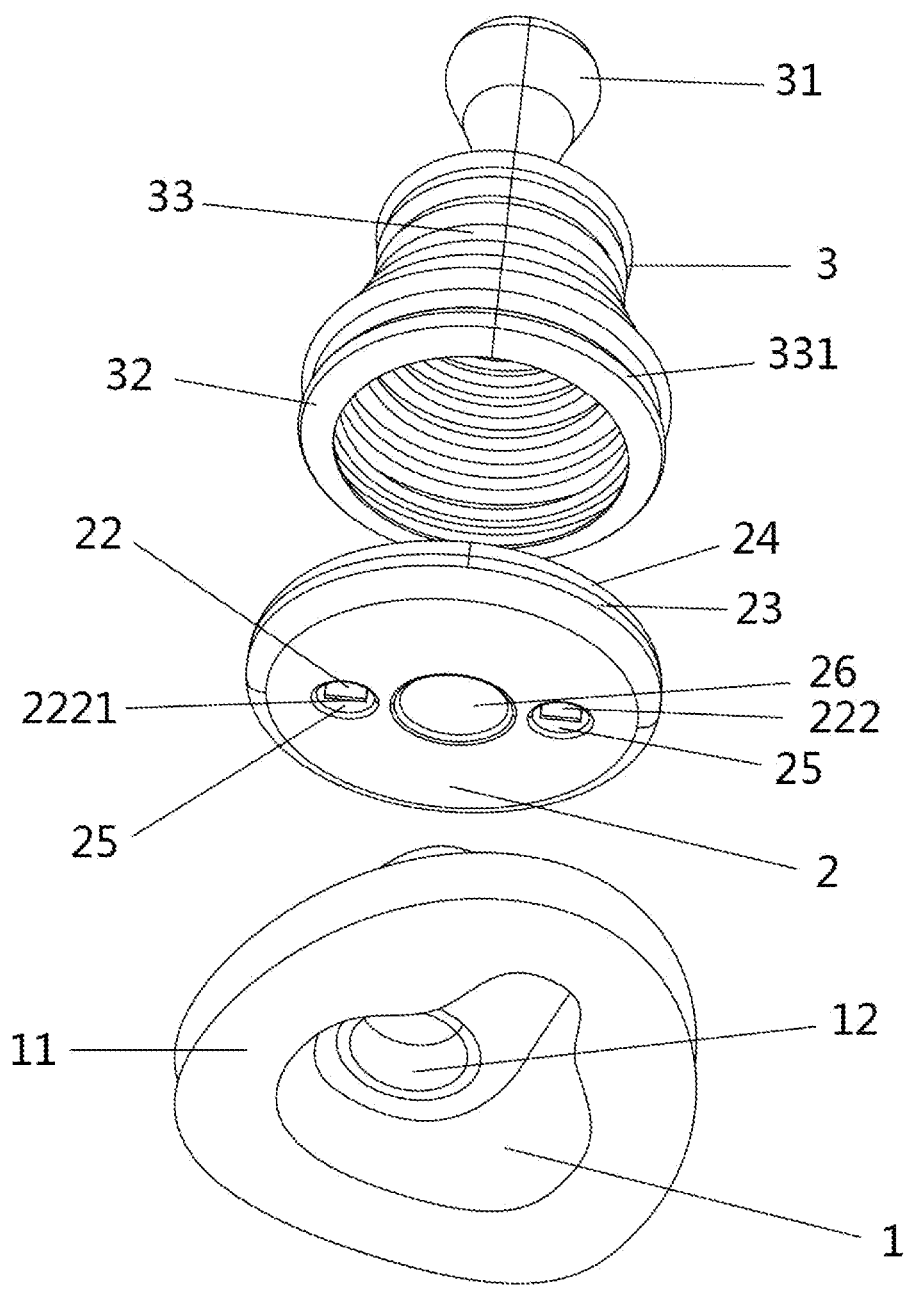
FIG. 2 is a three-dimensional exploded schematic diagram (I) of the removal device provided in this embodiment.
Figure 3:
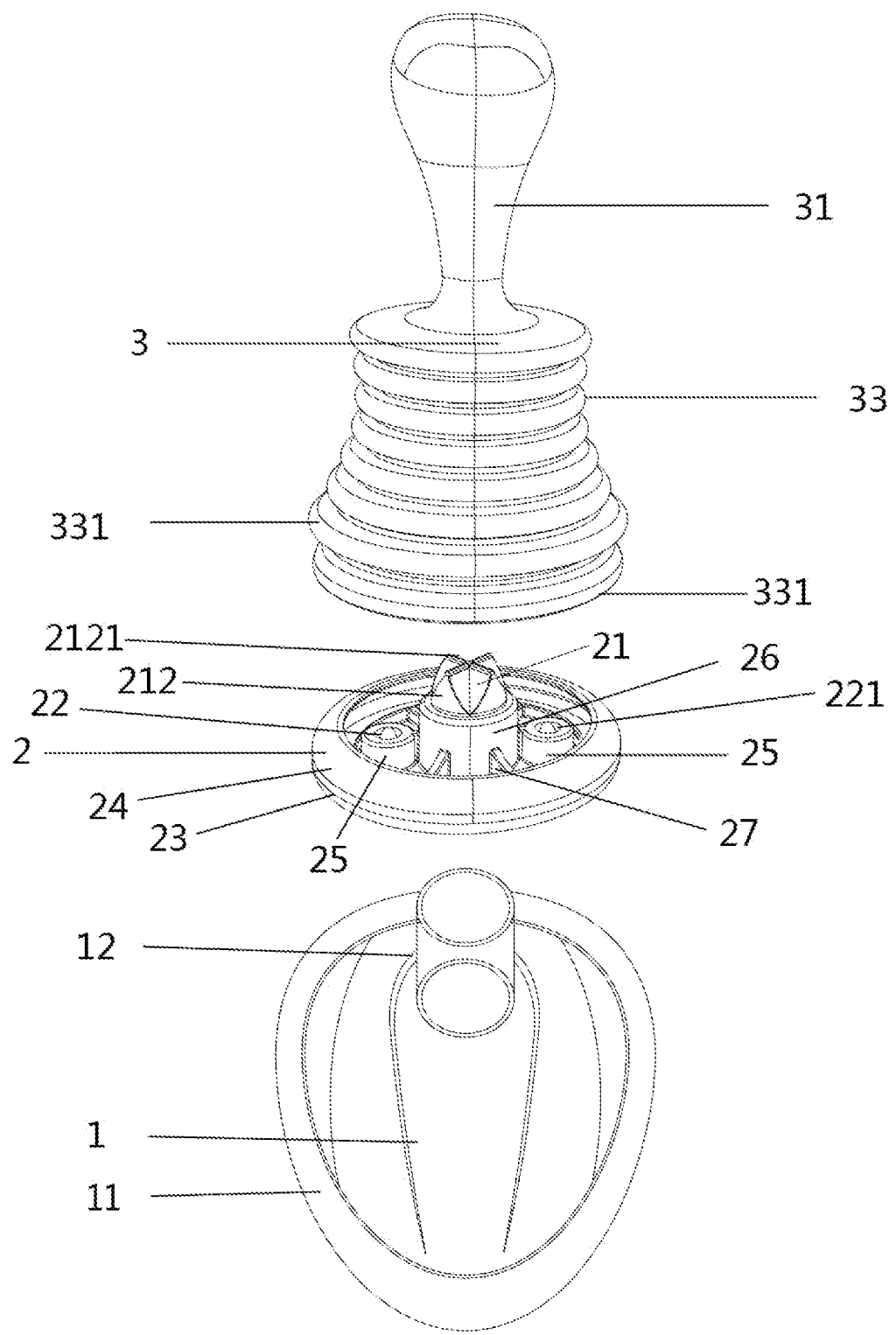
FIG. 3 is a three-dimensional exploded schematic diagram (II) of the removal device provided in this embodiment.
Figure 4:
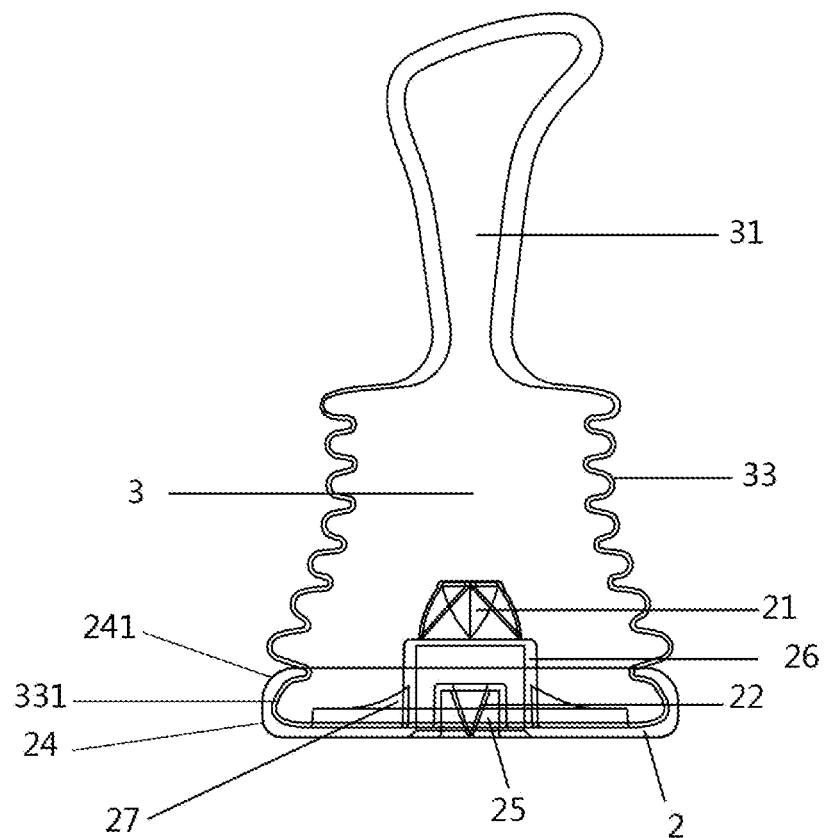
FIG. 4 is a combined schematic diagram of a connector and a collapsible gasbag provided in this embodiment.

This embodiment provides a removal device for removing an obstruction in a respiratory tract. With reference to FIG. 1, FIG. 1 is a three-dimensional combined schematic diagram of a removal device provided in this embodiment. As shown in FIG. 1, the removal device comprises a collapsible gasbag 3, a connector 2 and a face mask 1 which are sequentially connected. With reference to FIG. 2, FIG. 2 is a three-dimensional exploded schematic diagram (I) of the removal device provided in this embodiment. As shown in FIG. 2, the collapsible gasbag 3 is internally provided with a gas storage cavity, the top of the collapsible gasbag 3 is sealed, and the bottom of the collapsible gasbag is provided with an opening 32 in communication with the gas storage cavity. In this embodiment, an upper side of the connector 2 is hermetically connected to the opening 32, with details shown in FIG. 3. FIG. 3 is a three-dimensional exploded schematic diagram (II) of the removal device provided in this embodiment. As shown in FIG. 3, the connector 2 is made from an elastic material, and is provided with a bottom plate 23, an upper side of the bottom plate 23 is provided with an annular first peripheral side wall 24, an upper end of the first peripheral side wall 24 shrinks inward to form a stop edge 241, the collapsible gasbag 3 is provided with a second peripheral side wall 33 made from an elastic material, and the second peripheral side wall 33 is provided with a plurality of layers of outwardly convex folds. The inner diameter of the stop edge 241 is smaller than the lowermost fold 331 of the collapsible gasbag 3. Since both the collapsible gasbag 3 and the connector 2 are made from the elastic material, the lowermost fold 331 of the collapsible gasbag 3 may be deformed to enter a bayonet defined by the stop edge 241. The collapsible gasbag 3 is not provided with a vent hole which is in direct communication with the outside. With reference to FIG. 4, FIG. 4 is a combined schematic diagram of the connector 2 and the collapsible gasbag 3 provided in this embodiment. As shown in FIG. 4, when the connector 2 and the collapsible gasbag 3 are connected and combined, the second peripheral side wall 33 is inserted into the first peripheral side wall 24, the first peripheral side wall 24 covers the lowermost fold 331 of the second peripheral side wall 33, and the stop edge 241 covers an upper side of the lowermost fold 331. Therefore, the connector 2 and the collapsible gasbag 3 are guaranteed to be connected stably, so as to prevent the connector 2 from being separated from the collapsible gasbag 3. In addition, the outer side of the second peripheral side wall 33 is closely attached to the inner side of the first peripheral side wall 24, so as to guarantee desirable gas impermeability between the connector 2 and the collapsible gasbag 3. In this embodiment, the connector 2 is provided with a first check valve 21, and a first gas outlet end of the first check valve 21 is in communication with the gas storage cavity, with details shown in FIG. 3. The bottom plate 23 is provided with a central cylinder 26 which is vertically through and encircled by the first peripheral side wall 24; the first check valve 21 is of a hollowed structure made from an elastic material, and comprises a deformed portion 212 and a first base portion which are connected to each other; and the first gas outlet end is composed of four first slits 2121 provided at a top end of the deformed portion 212, the four first slits 2121 being in the shape of a cross, and one ends, extending toward the center, of the four first slits 2121 intersecting at the same point. Certainly, in some other embodiments, the number of the first slits 2121 on the first check valve 21 may be 3, 5 or 6, etc. The first gas inlet end is a first vent hole provided in the middle of the first base portion. The first base portion extends into the central cylinder 26, and the outer side of the first base portion is hermetically connected to the inner side of the central cylinder 26; and a lower end of the central cylinder 26 is hermetically connected to an upper side of the face mask 1. The deformation portion is exposed out of the central cylinder 26 and extends into the gas storage cavity. It may be understood that when gas flows into the deformation portion through the first vent hole, pressure in the deformation portion gradually increases such that the deformation portion is deformed by expansion, so that the four first slits 2121 are opened, thereby allowing the gas on the side of the first vent hole to flow into the gas storage cavity; and when the gas flowing into the deformation portion through the first vent hole is reduced or disappears, pressure in the deformation portion is reduced and even reduced to zero, and the deformation portion shrinks under its own elasticity such that the four first slits 2121 are closed, thereby preventing the gas in the gas storage cavity from flowing out of the first vent hole. In this embodiment, the connector 2 is further provided with a second check valve 22, a second gas inlet end of the second check valve 22 is in communication with the gas storage cavity, and a second gas outlet end of the second check valve is in communication with the outside. Still referring to FIG. 3 for details, the bottom plate 23 is provided with a peripheral cylinder 25 which is vertically through and encircled by the first peripheral side wall 24. The second check valve 22 is a duckbill valve, the second check valve 22 comprises a duckbill portion 222 and a second base portion 221 which are connected to each other, the second gas inlet end is a second vent hole provided in the middle of the second base portion 221, and the second gas outlet end is a second slit 2221 provided in the duckbill portion 222. The outer side of the second base portion 221 is hermetically connected to the inner side of the peripheral cylinder 25, and the second vent hole of the second base portion 221 is in communication with the gas storage cavity. With reference to FIG. 2, the duckbill portion 222 extends into the peripheral cylinder 25, and a lower end of the peripheral cylinder 25 is in communication with the outside. It may be understood that when gas flows into the duckbill portion through the second vent hole, pressure in the duckbill portion 222 gradually increases such that the duckbill portion 222 is deformed by expansion, so that the second slit 2221 is opened, thereby allowing gas in the gas storage cavity to be discharged to the outside. When gas flowing into the duckbill portion through the second vent hole is reduced or disappears, pressure in the deformation portion is reduced and even reduced to zero, and the duckbill portion 222 shrinks under its own elasticity such that the second slit 2221 is closed, thereby preventing outside gas from flowing into the gas storage cavity through the second vent hole. In this embodiment, an upper side of the face mask 1 is hermetically connected to a first gas inlet end of the first check valve 21. With reference to FIG. 3 for details, the upper side of the face mask 1 is provided with a connecting cylinder 12 which is vertically through in the middle. When the face mask 1 and the connector 2 are combined, the connecting cylinder 12 is inserted into the inner side of the lower end of the central cylinder 26 from bottom to top, and the outer side of the connecting cylinder 12 is hermetically connected to the inner side of the central cylinder 26. With reference to FIG. 2 and FIG. 3, a lower side of the face mask 1 is provided with a flexible annular pad 11 attached to a face.

When the removal device provided in this embodiment is used for rescuing a choked patient, the flexible annular pad 11 of the face mask 1 encircles a mouth of the choked patient and is closely attached to a face so as to be connected to a respiratory tract of the patient; and then, the face mask 1 is held with one hand to keep a seal between the face mask 1 and the face, and the collapsible gasbag 3 is pressed downward and stretched with the other hand repeatedly, such that the obstruction in the respiratory tract of the patient may be extracted out quickly. It should be explained that in the process of compressing the collapsible gasbag 3, gas flows from the inside of the collapsible gasbag 3 to the outside of the collapsible gasbag 3 at the second check valve 22, and the first check valve 21 is tightly closed, that is, gas in the gas storage cavity may be discharged to the outside through the second check valve 22, but may not enter the respiratory tract of the patient through the first check valve 21. In the process of stretching the collapsible gasbag 3, the volume of the gas storage cavity increases, the second slit 2221 of the second check valve 22 is tightly closed, so as to prevent the outside gas from flowing into the gas storage cavity, and thus form negative pressure in the gas storage cavity, that is, gas pressure in the gas storage cavity is lower than gas pressure in the respiratory tract of the patient, gas flows from the outside of the collapsible gasbag 3 to the inside of the collapsible gasbag 3 at the first check valve 21, such that the gas pressure in the respiratory tract may push the obstruction outward, and thus discharge the obstruction out of the first check valve 21 into the collapsible gasbag 3, and the closed collapsible gasbag 3 may collect some debris from an oral cavity and esophagus to avoid residual backflow in the collapsible gasbag 3.

To sum up, by using the removal device, the patient suffering from respiratory tract obstruction and choking may be rescued quickly and effectively only by repeating simple stretching operations. Therefore, under the condition that the "Heimlich Maneuver" rescue method may not be effectively implemented, we may utilize the removal device to quickly and effectively rescue the patient with the respiratory tract obstruction and choking. In addition, if your own respiratory tract suffers obstruction and choking, the removal device may be utilized for effective self-rescue without the help of others around.

It should be pointed out that in the process of compressing the collapsible gasbag 3, the gas in the gas storage cavity of the collapsible gasbag 3 is compressed, gas pressure in the gas storage cavity increases, and the deformation portion of the first check valve 21 is pressed and compressed further, such that the first slit 2121 of the first check valve 21 is closed more tightly, and the gas in the gas storage cavity is better prevented from flowing into the respiratory tract of the patient through the first check valve 21. Similarly, in the process of stretching the collapsible gasbag 3, gas pressure in the gas storage cavity decreases, and the duckbill portion 222 of the second check valve 22 is further contracted under the action of the outside gas pressure, such that the second slit 2221 of the second check valve is closed more tightly, and outside gas is better prevented from flowing into the gas storage cavity, which is conducive to forming higher and more stable negative pressure in the gas storage cavity.

It is worth mentioning that the deformation portion of the gas outlet end of the first check valve 21 is provided with four first slits 2121 in communication with one another, which makes it easier to open the gas outlet end of the first check valve 21 (compared with a common duckbill valve), and is conducive to extracting out the obstruction in the respiratory tract of the patient.

It should be noted that when the removal device is used, the flexible annular pad 11 may encircle the mouth (or the mouth and nose) of the choked patient at the same time. In addition, the flexible annular pad 11 may be suitable for different face types, such that the face mask 1 may be closely attached to the faces of different patients, and desirable gas impermeability between the face mask 1 and the face of the patient is ensured. In addition, the flexible annular pad 11 may be used as a buffer during compression, so as to avoid injury to the face of the patient.

Further, the connector 2 is an integrally formed member made from an elastic material. That is, the bottom plate 23, the first peripheral side wall 24, the central cylinder 26, the peripheral cylinder 25, the first check valve 21 and the second check valve 22 are integrally formed. In this way, the gas impermeability of the connector 2 itself may be ensured, and therefore stable negative pressure may be formed in the gas storage cavity.

Further, the face mask 1, the connector 2 and the collapsible gasbag 3 are integral, and the face mask 1, the connector 2 and the collapsible gasbag 3 are non-detachable, which does not need assembly before use, and facilitates immediate use. In addition, the phenomenon that the face mask 1, the connector 2 and the collapsible gasbag 3 are separated from one another during use is prevented.

Further, with reference to FIG. 3, the connector 2 is provided with a plurality of second check valves 22, the plurality of second check valves 22 encircling the first check valve 21. Herein, by arranging the plurality of second check valves 22, the discharge velocity of the gas in the gas storage cavity may be accelerated when the collapsible gasbag 3 is compressed, which is conducive to improving the efficiency of downward pressing of the collapsible gasbag 3.

Further, with reference to FIG. 3, a plurality of reinforcement strips 27 are arranged on the upper side of the bottom plate 23, two opposite ends of each reinforcement strip 27 being separately connected to the inner side of the first peripheral side wall 24 and the outer side of the central cylinder 26. Herein, the reinforcement strip 27 plays a role in stabilizing the connector 2, increasing the hardness of the connector 2, and therefore avoiding the situation that the first check valve 21 or the second check valve 22 deforms or components are not connected stably due to excessive deformation of the connector 2.

Further, a top wall of the collapsible gasbag 3 is connected to a handle 31 for holding. In this way, the handle 31 may be held to press or stretch the collapsible gasbag 3, facilitating application of force by a rescuer. Certainly, in some other embodiments, the handle 31 may also be replaced with a knob, which is also conducive to downward pressing and pulling operation on the collapsible gasbag 3 by the rescuer.

The embodiments of the disclosure have been described above with reference to the drawings, but the disclosure is not limited to the above detailed description. The above detailed description is only schematic, not limiting. Under the enlightenment of the disclosure, those of ordinary skill in the art can make many forms without departing from the spirit of the disclosure and the scope of protection of the claims, all of which fall within the protection of the disclosure.

The invention claimed is:

1. A removal device for removing an obstruction in a respiratory tract, the removal device comprising a collapsible gasbag, a connector and a face mask which are sequentially connected,
wherein the collapsible gasbag is internally provided with a gas storage cavity, a top of the collapsible gasbag is sealed, and a bottom of the collapsible gasbag is provided with an opening in communication with the gas storage cavity;

an upper side of the connector is hermetically connected to the opening, and the connector is provided with a first check valve and a second check valve, a first gas outlet end of the first check valve is in communication with the gas storage cavity, a second gas inlet end of the second check valve is in communication with the gas storage cavity, and a second gas outlet end of the second check valve is in communication with the outside; and an upper side of the face mask is hermetically connected to a first gas inlet end of the first check valve, and a lower side of the face mask is provided with a flexible annular pad configured to attach to a face, wherein the connector comprises a bottom plate and the first check valve and the second check valve are arranged on the bottom plate, wherein the first check valve and the second check valve allow gas flow to pass in opposite directions.

2. The removal device for removing the obstruction in the respiratory tract according to claim 1, wherein the connector is provided with a plurality of second check valves, the plurality of second check valves encircling the first check valve.

3. A removal device for removing an obstruction in a respiratory tract, the removal device comprising a collapsible gasbag, a connector and a face mask which are sequentially connected,
wherein the collapsible gasbag is internally provided with a gas storage cavity, the top of the collapsible gasbag is sealed, and the bottom of the collapsible gasbag is provided with an opening in communication with the gas storage cavity;

an upper side of the connector is hermetically connected to the opening, and the connector is provided with a first check valve and a second check valve; a first gas outlet end of the first check valve is in communication with the gas storage cavity, a second gas inlet end of the second check valve is in communication with the gas storage cavity, and a second gas outlet end of the second check valve is in communication with the outside; and an upper side of the face mask is hermetically connected to a first gas inlet end of the first check valve, and a lower side of the face mask is provided with a flexible annular pad configured to attach to a face, wherein the connector is provided with a bottom plate, the bottom plate being provided with a central cylinder which is vertically through; the first check valve is of a hollowed structure made from an elastic material, and comprises a deformed portion and a first base portion which are connected to each other; the first gas outlet end is composed of at least three first slits provided at a top end of the deformed portion; one end, extending toward the center, of the at least three first slits intersect at the same point, and the first gas inlet end is a first vent hole provided in the middle of the first base portion; the first base portion extends into the central cylinder, and an outer side of the first base portion is hermetically connected to an inner side of the central cylinder; a lower end of the central cylinder is hermetically connected to an upper side of the face mask; the deformation portion is exposed out of the central cylinder and extends into the gas storage cavity; when gas flows into the deformation portion through the first vent hole, pressure in the deformation portion gradually increases such that the deformation portion is deformed by expansion, so that the at least three first slits are opened, thereby allowing the gas on the side of the first vent hole to flow into the gas storage cavity; and when the gas flowing into the deformation portion through the first vent hole is reduced or disappears, pressure in the deformation portion is reduced and even reduced to zero, and the deformation portion shrinks under its own elasticity such that the three first slits are closed, thereby preventing the gas in the gas storage cavity from flowing out of the first vent hole.

4. The removal device for removing the obstruction in the respiratory tract according to claim 3, wherein the upper side of the face mask is provided with a connecting cylinder which is vertically through in the middle, the connecting cylinder being inserted into the inner side of the lower end of the central cylinder from bottom to top, and an outer side of the connecting cylinder being hermetically connected to the inner side of the central cylinder.

5. The removal device for removing the obstruction in the respiratory tract according to claim 3, wherein an upper side of the bottom plate is provided with a first peripheral side wall encircling the central cylinder, an upper end of the first peripheral side wall shrinking inward to form a stop edge; the collapsible gasbag is provided with a second peripheral side wall made from an elastic material, the second peripheral side wall being provided with a plurality of layers of outwardly convex folds; and the first peripheral side wall covers the lowermost fold of the second peripheral side wall, and the stop edge covers an upper side of the lowermost fold.

6. The removal device for removing the obstruction in the respiratory tract according to claim 5, wherein a plurality of reinforcement strips are arranged on the upper side of the bottom plate, two opposite ends of each reinforcement strip being separately connected to the inner side of the first peripheral side wall and the outer side of the central cylinder.

7. The removal device for removing the obstruction in the respiratory tract according to claim 1, wherein a top wall of the collapsible gasbag is connected to a handle for holding.

8. The removal device for removing the obstruction in the respiratory tract according to claim 3, wherein four first slits are provided, the four first slits being in the shape of a cross.

9. A removal device for removing an obstruction in a respiratory tract, the removal device comprising a collapsible gasbag, a connector and a face mask which are sequentially connected,
wherein the collapsible gasbag is internally provided with a gas storage cavity, the top of the collapsible gasbag is sealed, and the bottom of the collapsible gasbag is provided with an opening in communication with the gas storage cavity;
an upper side of the connector is hermetically connected to the opening, and the connector is provided with a first check valve and a second check valve; a first gas outlet end of the first check valve is in communication with the gas storage cavity, a second gas inlet end of the second check valve is in communication with the gas storage cavity, and a second gas outlet end of the second check valve is in communication with the outside; and
an upper side of the face mask is hermetically connected to a first gas inlet end of the first check valve, and a lower side of the face mask is provided with a flexible annular pad configured to attach to a face,
wherein the connector is provided with a bottom plate, the bottom plate being provided with a peripheral cylinder which is vertically through; the second check valve is a duckbill valve, the second check valve comprises a duckbill portion and a second base portion which are connected to each other, the second gas inlet end is a second vent hole provided in the middle of the second base portion, and the second gas outlet end is a second slit provided in the duckbill portion; an outer side of the second base portion is hermetically connected to an inner side of the peripheral cylinder, and the second vent hole of the second base portion is in communication with the gas storage cavity; the duckbill portion extends into the peripheral cylinder, and a lower end of the peripheral cylinder is in communication with the outside; when gas flows into the duckbill portion through the second vent hole, pressure in the duckbill portion gradually increases such that the duckbill portion is deformed by expansion, so that the second slit is opened, thereby allowing gas in the gas storage cavity to be discharged to the outside; and when gas flowing into the duckbill portion through the second vent hole, pressure in the deformation portion is reduced and even reduced to zero, and the duckbill portion shrinks under its own elasticity such that the second slit is closed, thereby preventing outside gas from flowing into the gas storage cavity through the second vent hole.

10. The removal device for removing the obstruction in the respiratory tract according to claim 1, wherein the connector is an integrally formed member made from an elastic material.

11. The removal device for removing the obstruction in the respiratory tract according to claim 1, wherein the face mask, the connector and the collapsible gasbag are integral.

12. The removal device for removing the obstruction in the respiratory tract according to claim 1, wherein the collapsible gasbag is not provided with a vent hole which is in direct communication with the outside.

13. A connector for a removal device, the connector comprising a bottom plate, and a first check valve and a second check valve which are arranged on the bottom plate, wherein the first check valve and the second check valve allow gas flow to pass in opposite directions; and the connector is an integrally formed member made from an elastic material.

14. The connector according to claim 13, wherein the connector is provided with one first check valve and a plurality of second check valves, the plurality of second check valves encircling the first check valve.

15. The connector according to claim 14, wherein the bottom plate is provided with a central cylinder which is vertically through; the first check valve is of a hollowed structure and comprises a deformed portion and a first base portion which are connected to each other, and a first gas outlet end and a second vent hole of the first check valve are provided in the deformed portion and the first base portion respectively; the first gas outlet end is composed of at least three first slits provided at a top end of the deformed portion, one ends, extending toward the center, of the at least three first slits intersecting at the same point; and the first gas inlet end is a first vent hole provided in the middle of the first base portion.

16. The connector according to claim 15, wherein the second check valve is a duckbill valve, the second check valve comprises a duckbill portion and a second base portion which are connected to each other, and a second gas outlet end and a second gas inlet end of the second check valve are provided in the duckbill portion and the second base portion respectively; the second gas inlet end is a second vent hole provided in the middle of the second base portion, and the second gas outlet end is a second slit provided in the duckbill portion; and the duckbill portion and the deformed portion separately face two opposite sides of the bottom plate.

17. The connector according to claim 15, wherein the removal device is configured to remove an obstruction in a respiratory tract, the removal device comprising a collapsible gasbag, the connector and a face mask which are sequentially connected, wherein the collapsible gasbag is internally provided with a gas storage cavity, the top of the collapsible gasbag is sealed, and the bottom of the collapsible gasbag is provided with an opening in communication with the gas storage cavity;

an upper side of the connector is hermetically connected to the opening; the first gas outlet end of the first check valve is in communication with the gas storage cavity, a second gas inlet end of the second check valve is in communication with the gas storage cavity, and a second gas outlet end of the second check valve is in communication with the outside; and an upper side of the face mask is hermetically connected to the first gas inlet end of the first check valve, and a lower side of the face mask is provided with a flexible annular pad configured to attach to a face.

* * * * *